United States Patent [19]

Audia

[11] Patent Number: 5,430,157
[45] Date of Patent: Jul. 4, 1995

[54] REDUCED PHENANTHRENES

[75] Inventor: James E. Audia, Indianapolis, Ind.

[73] Assignee: Eli Lilly and Company, Indianapolis, Ind.

[21] Appl. No.: 166,482

[22] Filed: Dec. 13, 1993

[51] Int. Cl.$^6$ ............... C07D 257/04; C07C 205/05; C07C 61/28; A61K 31/41; A61K 31/19
[52] U.S. Cl. .................... 548/250; 560/55; 562/23; 562/622; 562/8; 562/405; 568/929
[58] Field of Search ............ 548/250; 560/55; 562/23, 622, 8, 405; 568/929; 514/381, 576, 557, 75, 740

[56] References Cited

U.S. PATENT DOCUMENTS 4,882,319  11/1989  Holt et al. .................. 514/119

FOREIGN PATENT DOCUMENTS 0343954  5/1989  European Pat. Off. ...... C07J 41/00
0465123  6/1991  European Pat. Off. ...... C07J 43/00
0465141  6/1991  European Pat. Off. ...... C07J 41/00
92/20700  5/1992  WIPO ..................... C07J 41/00

OTHER PUBLICATIONS

Holt et al., *J. Med. Chem.*, 33(3), 937/(1990).
Holt et al., *J. Med. Chem.*, 33, 943/(1990).
Levy et al., *Biochemistry*, 29, 2815/(1990).
Holt, et al., *Biorganic & Medicinal Chemistry Letters*, 3(8), 1735 (1993).

*Primary Examiner*—David B. Springer
*Attorney, Agent, or Firm*—Joseph A. Jones

[57] ABSTRACT

A series of tetrahydrophenanthrenes are useful as inhibitors of 5α-reductase.

15 Claims, No Drawings

REDUCED PHENANTHRENES

FIELD OF THE INVENTION

The present invention belongs to the fields of pharmaceutical chemistry and pharmacology, and provides reduced phenanthrenes which are pharmaceuticals for the inhibition of 5α-reductase.

BACKGROUND OF THE INVENTION

It is now widely known that certain undesirable physiological conditions such as benign prostatic hyperplasia, male pattern baldness, acne vulgaris, seborrhea, androgenic alopecia, hirsutism and prostate cancer are androgen mediated conditions dependent on 5α-dihydrotestosterone (DHT). The enzyme 5α-reductase mediates the conversion of testosterone to the more potent androgen DHT in various target organs. It has been demonstrated that inhibitors of 5α-reductase (5AR) should block the formation of DHT and ameliorate the above undesirable physiological conditions. At least one 5AR inhibitor, finasteride, is now in the marketplace and is approved for the treatment of benign prostatic hyperplasia. Mocellini, et al., *The Prostate* 22, 291–299 (1993).

Recently, it has been found that there are at least two 5AR isozymes in humans, Andersson, et al., *Proc. Natl. Acad. Sci. USA* 87, 3640–44 (1990); Andersson, et al., *Nature* 354, 159–61 (1991). The two isozymes exhibit some differences in their biochemical properties, genetics and pharmacology. The two 5AR isozymes (usually called type 1 and type 2) are now the subject of considerable research, which has not yet shown clearly the roles which each isozyme plays in the body.

The present invention provides a series of new compounds which are effective inhibitors of 5AR.

SUMMARY OF THE INVENTION

The present invention provides phenanthrenes of the formula

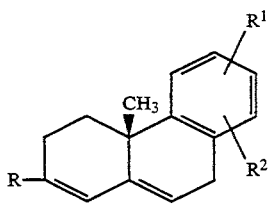

wherein
R represents carboxy, C$_1$–C$_4$ alkoxycarbonyl, hydroxyaminocarbonyl, phosphono, phosphino, nitro, etrazolyl, cyano or a leaving group;
R$^1$ and R$^2$ independently represent hydrogen, halo, trifluoromethyl, C$_1$–C$_4$ alkyl, —(CH$_2$)$_n$COR$^3$ or

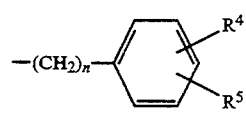

provided that no more than one of R$^1$ and R$^2$ represents hydrogen;
n represents 0–3;

R$^3$ represents hydroxy, C$_1$–C$_3$ alkyl, C$_1$–C$_3$ alkoxy, phenoxy, phenyl, amino, C$_1$–C$_3$ alkylamino or di(C$_1$–C$_3$ alkyl)amino;
R$^4$ and R$^5$ independently represent hydrogen, C$_1$–C$_4$ alkyl, halo or trifluoromethyl;
or a pharmaceutically acceptable salt of a compound of formula I wherein R is carboxy, phosphono or phosphino.

The invention also provides a method of inhibiting 5AR, particularly type II 5AR, in a patient in need of such treatment, comprising the administration of an effective 5AR-inhibiting amount of a compound of formula I wherein R represents hydroxyaminocarbonyl, tetrazolyl, carboxy, phosphono, phosphino or nitro to such a patient.

The invention further provides pharmaceutical compositions of the above-mentioned class of the compounds of formula I comprising pharmaceutically acceptable inert ingredients, and still further provides methods of treating benign prostatic hyperplasia, male pattern baldness, acne vulgaris, seborrhea, androgenic alopecia, hirsutism and prostatic cancer, comprising the administration of a compound of the above-mentioned class of the compounds of formula I to a patient in need of such treatment.

DETAILED DESCRIPTION OF THE INVENTION

Throughout the present document, all temperatures will be described in degrees Celsius, and all expressions of concenuration, percentage and proportion will be expressed in weight units, unless otherwise stated.

The compounds of formula I wherein the group R represents carboxy, phosphono, phosphino, hydroxyaminocarbonyl, nitro or tetrazolyl are pharmaceuticals useful for the inhibition of 5AR. The other compounds of formula I are intermediates useful in the preparation of the pharmaceuticals.

The terms "phosphono" and "phosphino" refer to the phosphorous containing groups, respectively

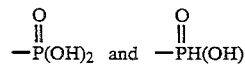

The tetrazolyl group is a 1-tetrazolyl.

The term "C$_1$–C$_4$ alkoxycarbonyl" refers to a carboxy group which has been esterified and carries a C$_1$–C$_4$ alkyl group such as methyl, ethyl, propyl, isopropyl, butyl or one of the three isomeric butyl groups.

The term "leaving group" refers to one of the substituents which are used by synthetic organic chemists to confer activity on a certain position of an organic molecule and which are readily replaced by other groups in a synthesis. Preferred leaving groups include, for example, methanesulfonyl, trifluoromethanesulfonyl, toluenesulfonyl, substituted toluenesulfonyl groups, bromo and iodo.

The compounds of formula I are reduced phenanthrenes, and the positions of the molecule are identified as follows:

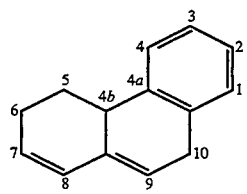

The reader will understand that many of the compounds of the present invention exist in more than one optically isomeric form. If no information is given about the optical form of a compound in this document, the racemic form and all optically isomeric forms are meant. When a specific optically isomeric form, or mixture of specific forms, is meant, the compound will be specifically so named or described.

It will be noted that the methyl substituent at the 4b-position must be in the optical configuration indicated.

Certain groups of the pharmaceuticals of formula I are preferred, and those groups will be set out individually. It will be understood that the various preferred groups may be combined to form additional, more limited preferred groups.

a) R represents carboxy;
b) R represents carboxy or tetrazolyl;
c) R represents phosphono, phosphino, hydroxyaminocarbonyl or nitro;
d) $R^1$ and $R^2$ independently represent hydrogen, halo, trifluoromethyl or $C_1$-$C_4$ alkyl;
e) $R^1$ and $R^2$ independently represent hydrogen, chloro, bromo, triflouromethyl, or $C_1$-$C_4$ alkyl; and
f) $R^1$ represents hydrogen.

Further, certain of the intermediate compounds of formula I are also preferred, and are set out as follows.

g) R represents $C_1$-$C_4$ alkoxycarbonyl;
h) R represents cyano;
i) R represents a leaving group;
j) $R^1$ and $R^2$ independently represent hydrogen, halo, trifluoromethyl or $C_1$-$C_4$ alkyl;
k) $R^1$ and $R^2$ independently represent hydrogen, chloro, bromo, triflouromethyl, or C1-C4 alkyl; and
l) $R^1$ represents hydrogen.

Those compounds of formula I wherein R represents carboxy, phosphono or phosphino are capable of forming salts with pharmaceutically acceptable bases, and such salts are included as an aspect of the invention. Such salts include, for example, the alkali metals such as potassium, lithium and especially sodium; the alkaline earth metals such as calcium and magnesium; and amine salts such as triethanolamine, triethylamine, propanolamine and the like. It will be readily understood by pharmaceutical chemists that such salts are readily prepared by reaction with the corresponding bases; such processes are carried out in an inert organic solvent or in an aqueous organic solvent, and usually represent a preferred final step in the preparation of the pharmaceutical compounds of formula I, since such salts are more likely to be crystalline than are the free base compounds themselves.

A group of exemplary substituents which can be represented by $R^4$ and $R^5$ will be specifically named, since those substitutents are indicated by general terms in formula I and the reader may need some additional exemplification and explanation.

hydrogen
chloro
bromo
trifluoromethyl
methyl
t-butyl
propyl
carboxy
2-carboxyethyl
acetyl
3-butyrylpropyl
methoxycarbonyl
2-(isopropoxycarbonyl)ethyl
phenoxycarbonyl
3-benzoylpropyl
aminocarbonyl
(methylamino)carbonylmethyl
3-(propylaminocarbonyl)propyl
dimethylaminocarbonyl
2-(ethylmethylaminocarbonyl)ethyl
phenyl
3,5-diethylphenyl
3-(4-isopropylphenyl)propyl
2-ethyl-4-fluorophenyl
3-t-butyl-5-trifluoromethylphenyl
4-iodo -2-propylphenyl
1-(3-iodo-4-acetylphenyl)ethyl
3-(4-butyl-3-isopropylphenyl)propyl
4-ethylphenyl
3-methyl-5-isobutylphenyl
2-bromo-5-propylphenyl
4-trifluoromethylphenyl
3-trifluoromethyl-4-chlorophenyl
3-isopropyl-4-trifluoromethylphenyl

SYNTHESIS

The compounds of formula I are conveniently prepared from (S)-4,4a,9,10-tetrahydro-4a-methyl-2(3H)-phenanthreneone, appropriately substituted to provide the $R^1$ and $R^2$ substituents. That intermediate is prepared according to Preparation 1, which follows.

The substituted 1-methyl-2-tetralones which are the ultimate starting materials are readily obtained in commerce or easily prepared by methods known to ordinarily skilled organic chemists.

The oxo group of the phenanthreneone intermediate is converted to a leaving group by reaction with the appropriate reagent. For example, if a sulfonate leaving group is desired, the reagent is the appropriate sulfonic anhydride. If the desired leaving group is an imide such as phthalimide or succinimide, the reagent is the corresponding imidoyl halide, for example, phthalimidoyl chloride. Such reactions are readily carried out in inert organic solvents, such as halocarbons, including dichloromethane and carbon tetrachloride, for example, or in aromatic solvents, such as toluene and benzene. In general, the reactions may be carried out at moderate temperatures in the range of from about $-20°$ to about $50°$. When a bromo or iodo leaving group is desired the phenanthreneone is treated with a reagent such as phosporus tribromide or triiodide in acetic acid.

In order to prepare a compound of formula I where R is carboxy, the leaving group is removed and converted to an atkoxycarbonyl by reaction with triphenylphosphine and an alkanol in the presence of a precious metal catalyst such as palladium acetate. The reaction can be carried out at ambient temperature and pressure, under an atmosphere of carbon monoxide. The alkoxycarbonyl group is cleaved with a strong base to liberate the desired carboxy R group. Alternatively, a carboxy group may be prepared from a bromo or iodo intermediate by halogen-metal exchange with an alkyllithium reagent, followed by trapping with carbon dioxide.

The compounds wherein R is hydroxyaminocarbonyl are readily prepared by reaction of the corresponding carboxy compound with hydroxylamine under conditions appropriate for amide formation.

A compound wherein R is tetrazolyl is obtained directly from the phenanthreneone intermediate by first reacting with a nitrile reagent, such as trimethylsilylcyanide, and then closing the tetrazolyl ring by reacting the resulting intermediate, where R is cyano, with an azide reagent, preferably, tributyltin azide. The cyananion reaction can be carried out at ambient temperature, preferably in the presence of a Lewis acid such as boron trifluoride. The cyclization is best carried out in an inert atmosphere at an elevated temperature, such as from about 50° to about 100°.

Compounds wherein R is phosphono are readily prepared from intermediates wherein R is bromo or triflate (trifluoromethanesulfonate) by reaction with a dialkyl phosphite, particularly dimethyl phosphite, mediated by palladium. Palladium tetra(triphenyl phosphine) is preferred. The reaction is carried out in base, such as a trialkylamine, at an elevated temperature. The resulting intermediate is then dealkylated, for example, with trimethylsilyl iodide or boron tribromide, to obtain the desired product. The dealkylation is best done in a haloalkane, such as chloroform, in acid conditions.

The compounds where R is phosphino are made from the same intermediates as above, by coupling with hypophosphorous acid, mediated by palladium as described in the paragraph above.

The compounds wherein R is nitro are prepared from the same intermediates as above by coupling with hexamethylditin $((CH_3)_3SnSn(CH_3)_3)$, mediated with palladium as described above. The resulting trimethyltin intermediate is then reacted with tetranitromethane in an inert solvent (such as haloalkanes, particularly carbon tetrachloride) at an elevated temperature to obtain the desired 7-nitro compound.

The following preparations and examples further illustrate the synthesis of compounds of formula I.

Preparation 1
(S)-7-chloro-4,4a,9,10-tetrahydro-4a-methyl-2-(3H)-phenanthreneone

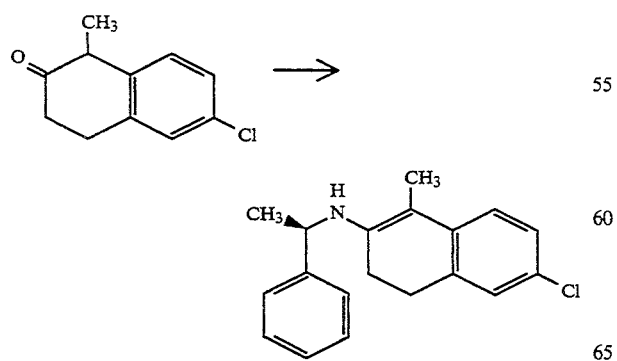

To a stirred solution of 6-chloro-1-methyl-2-tetralone (50.0 g, 0.256 mol.) in toluene (500 mL) was added (R)-(+)-1-phenethylamine (35 mL, 0.27 mol.). The solution was heated to reflux for 4 hours with azeotropic removal of water. The solution was allowed to cool to ambient temperature and was concentrated under reduced pressure to afford (R)-1-methyl-2-(1-methylbenzylamino)-6-chloro-3,4-dihydronaphthalene (79 g) as a yellow oil which was used without further purification.

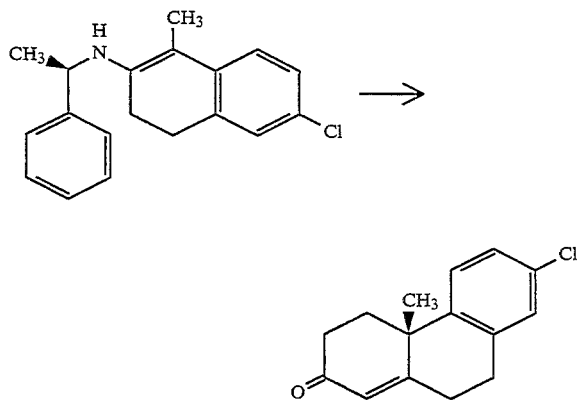

To a stirred solution of the above intermediate (79 g, 0.25 mol.) in tetrahydrofuran (500 mL) was added methyl vinyl ketone (23 mL, 0.28 mol.) in a single portion. The solution was stirred under nitrogen in the dark for 96 hours. Aqueous acetic acid (20%, 500 mL) was added and the solution stirred for 2 hours. The reaction mixture was partitioned between ethyl acetate and water. The organic phase was washed with saturated sodium carbonate solution and dried over anhydrous sodium sulfate. The solution was concentrated under reduced pressure and the resultant oil was dissolved in anhydrous ethanol (100 mL) and added to a stirred solution of sodium ethoxide, prepared by careful addition of sodium (6.5 g) to anhydrous ethanol (500 mL). The solution was heated at 50° C. for 3 hours, cooled to ambient temperature, and partitioned between diethyl ether and water. The organic phase was washed with brine and dried over anhydrous sodium sulfate. Removal of solvent under reduced pressure and chromatography of the residue on silica (eluting with 25% ethyl acetate in hexanes) afforded the title compound (34 g) as a brown oil which solidified upon standing.

Optical rotation: +15.39° at 589 nm; MS m/e=246; melting range 94°–96°.

Analysis Calculated for $C_{15}H_{15}C_{10}$ Theory C, 73.02%; H, 6.13%; Found C 72 73%; H 6.10%

Preparation 2
2-Chloro-7-(1,1,1-trifluoromethanesulfonytoxy)-4b-methyl-4b,5,6,10-tetrahydrophenanthrene

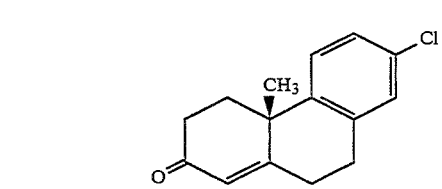

-continued

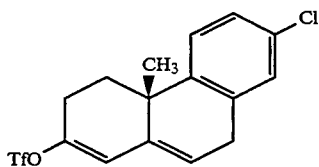

To a stirred solution of (S)-7-chloro-4,4a,9,10-tetrahydro-4a-methyl-2(3H)-phenanthreneone (1.64 g, 6.65 mmol.) in anhydrous dichloromethane was added 2,6-di-t-butylpyridine (3.3 mL, 14.6 mmol.) followed by triflic arthydride {2.25 mL, 13.3 mmol.). The solution was stirred at ambient temperature for 1 hour and concentrated under reduced pressure. The residue was taken up in 5% ethyl acetate in hexanes and washed with 1N sulfuric acid and with brine. The organic extracts were filtered through a plug of silica (eluting with 5% ethyl acetate in hexanes) and concentrated to afford the desired compound as a colorless oil (1.96 g) which was used without further purification.

Preparation 3

Methyl (—)-2-chloro-4b-methyl-4b,5,6,10-tetrahydrophenanthrene-7-carboxylate

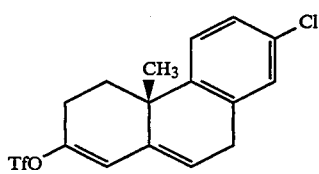

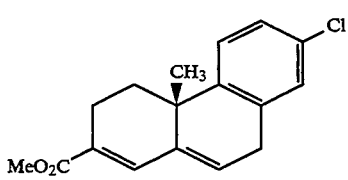

To a stirred solution of 2-chloro-7-(1,1,1-trifluoromethanesulfonyloxy)-4b-methyl-4b,5,6,10-tetrahydrophenanthrene (712 mg, 1.89 mmol.) in methanol (10 mL) and dimethylformamide (10 mL) was added triethylamine (526 μl, 3.75 mmol.) followed by triphenylphosphine (246 mg, 0.94 mmol.) and palladium acetate (106 mg, 0.47 mmol.). The solution was purged with carbon monoxide (3×) and stirred under CO atmosphere for 14 hours. The mixture was concentrated under reduced pressure and the residue partitioned between ethyl acetate and 1N sulfuric acid. The organic phase was dried over anhydrous magnesium sulfate and concentrated. The crude product was purified by chromatography on silica (eluting with 5% ethyl acetate in hexanes) to afford the desired compound (500 mg) as a pale oil.

EXAMPLE 1

(—)-2-Chloro-4b-methyl-4b,5,6,10-tetrahydrophenanthrene-7-carboxylic acid

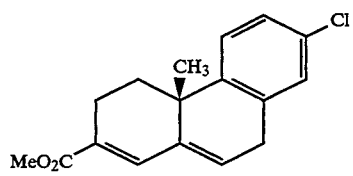

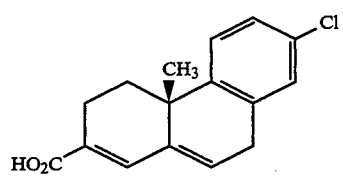

To a stirred solution of methyl (—)-2-chloro-4b-methyl-4b,5,6,10-tetrahydrophenanthrene-7-carboxylate (500 mg, 1.73 mmol.) in methanol (19 mL) and water (2 mL) was added potassium carbonate (300 mg). The solution was heated to reflux for 10 hours. The solution was allowed to cool to ambient temperature, was diluted with chloroform (100 mL) and was acidified with 1N sulfuric acid. The aqueous phase was further extracted with chloroform and the combined organic phases were dried over anhydrous magnesium sulfate. Removal of solvent under reduced pressure afforded crude acid as a yellow glass. The compound was purified by chromatography on silica (eluting with 25% ethyl acetate, 1% acetic acid in hexanes) to afford the title compound (396 mg) as a yellow crystalline solid.

mp 228°–230° C.
M/E=275
Analysis for $C_{16}H_{15}O_2Cl_1$: Calculated: C, 69.95; H, 5.50 Found: C, 69.92; H, 5.56
$\alpha[D]_{589} = -172.07$ (c=1.0, MeOH),
$\alpha[D]_{365} = -769.91$ (c=1.0, MeOH).

Preparation 4

(—)-2-Chloro-4b-methyl-4b,5,6,10-tetrahydrophenanthrene-7-carbonitrile

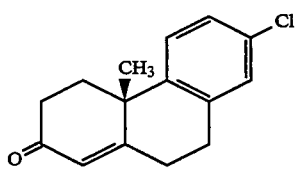

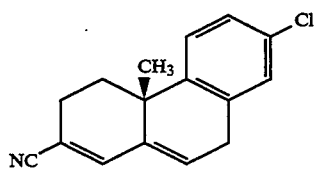

To a stirred solution of (S)-7-chloro-4,4a,9,10-metrahydro-4a-methyl-2(3H)-phenanthreneone (3.92 g, 15.89 mmol.), in benzene (50 mL) was added trimethylsilyl cyanide (2.54 mL, 19.1 mmol.) followed by boron trifluoride etherate (0.5 mL, 4.0 mmol.). The reaction mixture was stirred at ambient temperature for 2 hours. An additional portion of boron trifluoride etherate (0.5 mL, 4.0 mmol.) was added and the mixture stirred for 3 hours. Pyridine (10 mL) was added followed by phosphorus oxychloride (4.44 mL, 47.67 mmol.) and the solution heated to reflux for 5 hours. The solution was cooled to ambient temperature and poured onto ice-cooled 5N HCl. The mixture was extracted with diethyl ether (3×) and the combined ether extracts were washed with water and brine and dried over anhydrous magnesium sulfate and concentrated under reduced pressure. The crude product was purified by chromatography on silica gel, eluting with 5–15% ethyl acetate in hexanes. The product was further purified by crystallization from hexanes to afford 560 mg as yellow crystals.

EXAMPLE 2

(−)-2-Chloro-4b-methyl-4b,5,6,10-tetrahydro-phenanthrene-7-(1-tetrazole)

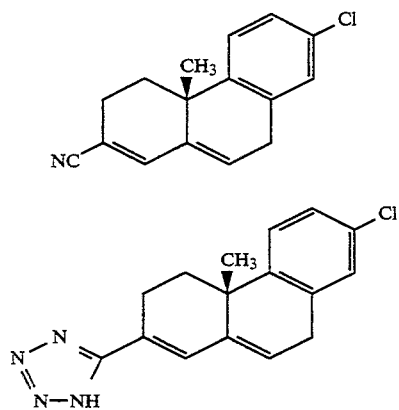

A mixture of (−)-2-chloro-4b-methyl-4b,5,6,10-tetrahydrophenanthrene-7-carbonitrile (100 mg, 0.39 mmol.) and tributyltin azide (800 mg, 2.41 mmol.) was heated under nitrogen atmosphere to about 80° for 6 hours. The mixture was cooled to ambient temperature and quenched with a solution of water, acetic acid and acetonitrile (1:1:8, 25 mL). After stirring for 1 hour, the mixture was washed with hexanes (2×) and diluted with ethyl acetate. The solution was washed with brine and dried over anhydrous sodium sulfate and concentrated under reduced pressure. The product was crystallized from ethyl acetate/hexanes to afford 100 mg as a light yellow crystalline solid.

M/E=298

Analysis for $C_{16}H_{15}N_4Cl_1$: Calculated: C, 64.32; H, 5.06; N, 18.75 Found: C, 64.41; H, 5.30; N, 18.67

$\alpha[D]_{589} = -86.78$ (c=1.0, MeOH), $\alpha[D]_{365} = -362.09$ (c=1.0, MeOH).

Compounds of the present invention have been shown to be inhibitors of 5AR in tests carried out according to the following method, which is adapted to routine use.

Methodology of Human Type II Steroid 5α-Reductase Assays

Preparation of Type II 5α-Reductase from Human Prostate:

Human prostate tissue from prostate surgeries was obtained immediately after surgery, frozen on dry ice and stored at −80° C. The tissue was frozen with liquid nitrogen and pulverized to powder. The powder was homogenized in ice-cold buffer (20 mM sodium phosphate, pH 6.5) using a Brinkmann Polvtron (Westbury, N.Y.) with a PTA 10-S probe and a setting of 7. The homogenization procedure consisted of four 15 second pulses. Connective tissue was cleared from the probe with forceps between pulses. The homogenate was then filtered through cheese cloth and the filtrate centrifuged at 100,000×g for one hour in a Beckman L8-60M ultracentrifuge. The pellet was resuspended by homogenization with a Dounce homogenizer using the same buffer solution, containing 20% glycerol. An aliquot was taken for protein determination by the Lowry method, Lowry, et al., Protein Measurement with the Folin Phenol Reagent, *J. Biol. Chem.*, 193, 265–75 (1951). Aliquots of the enzyme preparation were stored at −80° until use.

5α-Reductase Assay:

This enzyme assay is based on the conversion of [$^3$H]-testosterone to [$^3$H]-5α-dihydrotestosterone (DHT) and other 5α-reduced metabolites. While about 90% of the 5α-reduced metabolites formed in these assays was DHT, androstanedione was formed at about 10%. Essentially no androsterone was detected. In a total volume of 1.0 ml, the assay contained 2.6 μCi [$^3$H]-testosterone (50 nM), 500 μM of reduced nicotine adenine dinucleotide phosphate, 40 mM sodium acetate at pH 5.5, and test compounds as indicated. Test compounds were added in 20 μl of dimethylsulfoxide (20 μl of dimethylsulfoxide was added to blanks and controls). The reaction was initiated by the addition of 0.5 mg of Type II 5α-reductase. The reaction mixture was incubated for 30 min at 25° and terminated by the addition of 1 ml ice-cold stopping solution. The stopping solution contained 40 μM each of non-radioactive testosterone, DHT, androstenedione, androstanedione, androsterone, androstan-3β,17β-diol, and androstan-3α,17β-diol.

The samples were prepared for high performance liquid chromatography by solid phase extraction. Disposable solid matrix extraction columns (C-18 reversed phase, 6 ml, 500 mg; Bond Elut ™ from Analytichem international; Harbor City, Calif.) were conditioned by washing with 5 ml of methanol followed by 5 ml of deionized water. The reaction mixtures were then applied to the columns. The columns were subsequently washed with 5 ml of acetone:water (1:4), followed by 0.3 ml of methanol. The samples were then eluted with 3 ml of methanol and collected in 20 ml scintillation vials. Three ml of water was then added to each scintillation vial. The solutions were then transferred to tubes and centrifuged for 30 min at 1000×g to remove any particulate material before chromatography.

The [$^3$H]-testosterone substrate and its metabolites were separated by chromatography using a C-18 reversed phase column (Beckman Ultrasphere 5 μm spherical 80A pore, part no. 235329, 4.6 mm i.d.÷25 mm length) with an isocratic mobile phase (46 water: 46 methanol: 8 tetrahydrofuran by volume). The column temperature was maintained at 35° and the flow rate was 1.5 ml/min. A 400 μl aliquot was injected onto the column and radioactivity was determined using a Beckman 171 in-line flow radioisotope detector in conjunction with Rainin Dynamax ™ software and a Macintosh computer. The flow rate of the Atomflow ™ scintillation fluid was 4.5 ml/min.

The results of the assays on representative compounds are reported here as the 50% inhibitory concentration of each compound, compared to control reaction mixtures.

| Example 1 | 150 nanomolar |
| Example 2 | 600 nanomolar |

As noted above, the compounds of the present invention are useful for inhibiting the conversion of uestosterone to 5α-dihydrotestosterone. Therefore, another embodiment of the present invention is a method for inhibiting 5α-reductase by administering to a mammal in need of 5α-reductase inhibition a 5α-reductase inhibiting dose (effective amount) of a pharmaceutical compound according to Formula I.

The term "effective amount" as used herein means an amount of a compound of the present invention which is capable of inhibiting the conversion of testosterone to 5α-dihydrotestosterone which is catalyzed by the enzyme 5α-reductase and particularly, inhibiting 5α-reductase. The 5α-reductase inhibition contemplated by the present method includes both medical therapeutic and/or prophylactic treatment, as appropriate. The specific dose of compound administered according to this invention to obtain therapeutic and/or prophylactic effects will, of course, be determined by the particular circumstances surrounding the case, including, for example, the compound administered, the route of administration, and the condition being treated. A typical daily dose will contain a nontoxic dosage level of from about 0.01 mg/kg to about 50 mg/kg of body weight of the active compound of this invention. Preferred daily doses generally will be from about 0.05 to about 20 mg/kg and most preferably from about 0.1 to about 10 mg/kg.

A variety of physiologic functions have been associated with 5α-dihydrotestosterone. The compounds of this invention are therefore believed to have the ability to treat in mammals a variety of disorders associated with 5α-dihydrotestosterone including benign prostatic hyperplasia (or hypertrophy), male pattern baldness, acne vulgaris, hirsutism and prostatic cancer. Therefore, the present invention also provides methods of treating the above disorders at the rates set forth above for inhibiting the 5α-reductase catalyzed conversion of testosterone to 5α-dihydrotestosterone.

The compounds can be administered by a variety of routes including oral, rectal, transdermal, subcutaneous, intravenous, intramuscular, intranasal, and topical for male pattern baldness, ache vulgaris, and hirsutism. The compounds of the present invention are preferably formulated prior to administration. Therefore, another embodiment of the present invention is a pharmaceutical formulation comprising an effective amount of a compound of Formula I and a pharmaceutically acceptable carrier, diluent or excipient therefor.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be admixed with a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like. Typical formulations designed for topical administration are ointments, creams, gels, and lotions containing, for example, up to 10% by weight of the active compound.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example, anhydrous lanolin. Customarily, following formation of the base, whether oleaginous or absorbent, the active ingredient is added in an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia, colloidal clays, veegum, and the like. Upon formation of the emulsion, the active ingredient customarily is added in an amount to achieve the desired concentration.

Gels comprise a base selected from an oleaginous base, water, or an emulsion-suspension base, such as described above. To the base is added a gelling agent which forms a matrix in the base, increasing its viscosity. Examples of gelling agents are hydroxypropylcellulose, acrylic acid polymers, and the like. Customarily, the active ingredient is added to the formulation at the desired concentration at a point preceding addition of the gelling agent.

The following formulation examples are illustrative only and are not intended to limit the scope of the invention in any way.

Formulation 1

Hard gelatin capsules are prepared using the following ingredients

|  | Quantity (mg/capsule) |
|---|---|
| (−)-1,4-Dichloro-4b-methyl--7-nitro-4b,5,6,10-tetrahydrophenanthrene | 250 |
| Starch, dried | 200 |
| Magnesium stearate | 10 |
| Total | 460 mg |

Formulation 2

A tablet is prepared using the ingredients below:

|  | Quantity (mg/capsule) |
|---|---|
| Sodium (+)-4b-methyl-3-trifluoromethyl-4b,5,6,10- | 250 |

|  | Quantity (mg/capsule) |
|---|---|
| tetrahydrophenanthrene-7-phosponate | |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
|---|---|
| Potassium (+)-2-(4-chlorobenzyl)-4,4b-dimethyl-4b,5,6,10-tetrahydrophenanthrene-7-carboxylate | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Triethylamino (-)-3-(2-phenoxycarbonylethyl)-4b-methyl-4b,5,6,10-tetrahydrophenanthrene-7-carboxylate | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

| (−)-3-Chloro-4b-methyl-2-trifluoromethyl-4b,5,6,10- | 80 mg |
|---|---|
| tetrahydrophenanthrene-7-(1-tetrazole) | |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatine capsules in 200 mg quantities.

Formulation 6

Suppositories, each containing 225 mg of active ingredient, are made as follows:

| (+)-7-Hydroxyaminocarbonyl-1-propyl-3-(3-trifluoromethylphenyl)-4b-methyl-4b,5,6,10-tetrahydrophenanthrene | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| (−)-2-Methylaminocarbonylmethyl-4b-methyl-4b,5,6,10-tetrahydrophenanthrene-7-carboxylic acid | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| (+)-3-(3-Carboxypropyl)-4b-methyl-7-nitro-4b,5,6,10-tetrahydrophenanthrene | 100 mg |
|---|---|
| Isotonic saline | 1,000 ml |

The solution of the above ingredients generally is administered intravenously to a subject at a rate of 1 ml per minute.

The amount of active ingredient incorporated into the formulation of this invention is not critical; the concentration should only be in a range sufficient to permit ready administration of the formulation in an amount which will deliver the desired amount of active ingredient.

I claim:

1. A compound of the formula I

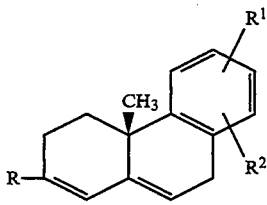

wherein

R represents carboxy, hydroxyaminocarbonyl, phosphono, phosphino, nitro, tetrazolyl;

$R^1$ and $R^2$ independently represent hydrogen, halo, trifluoromethyl, $C_1$-$C_4$ alkyl, —$(CH_2)_n COR^3$ or

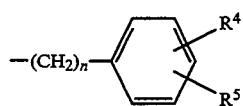

provided that no more than one of $R^1$ and $R^2$ represents hydrogen;

n represents 0–3;

$R^3$ represents hydroxy, $C_1$-$C_3$ alkyl, $C_1$-$C_3$ alkoxy, phenoxy, phenyl, amino, $C_1$-$C_3$ alkylamino or di($C_1$-$C_3$ alkyl)amino;

$R^4$ and $R^5$ independently represent hydrogen, $C_1$-$C_4$ alkyl, halo or trifluoromethyl;

or a pharmaceutically acceptable salt of a compound of formula I wherein R is carboxy, phosphono or phosphino.

2. A compound of claim 1 wherein R is carboxy, nitro, or tetrazolyl or a pharmaceutically acceptable salt thereof.

3. A compound of claim 1 wherein $R^1$ and $R^2$ independently represent hydrogen, halo, trifluoromethyl, or $C_1$-$C_4$ alkyl or a pharmaceutically acceptable salt thereof.

4. A compound of claim 2 wherein $R^1$ and $R^2$ independently represent hydrogen, halo, trifluoromethyl, or $C_1$-$C_4$ alkyl or a pharmaceutically acceptable salt thereof.

5. A compound of claim 3 wherein $R^1$ represents hydrogen or a pharmaceutically acceptable salt thereof.

6. The compound of claim 1 which is 2-chloro-4b-methyl-4b,5,6,10-tetrahydrophenanthrene-7-carboxylic acid, or a pharmaceutically acceptable salt thereof.

7. The compound of claim 1 which is 2-chloro-4b-methyl-4b,5,6,10-tetrahydrophenanthrene-7-(1-tetrazole).

8. A pharmaceutical composition comprising a pharmaceutically acceptable carrier, diluent or excipient, and a compound of claim 1.

9. A pharmaceutical composition comprising a pharmaceutically acceptable carrier, diluent or excipient, and a compound of claim 2.

10. A pharmaceutical composition comprising a pharmaceutically acceptable carrier, diluent or excipient, and a compound of claim 3.

11. A pharmaceutical composition comprising a pharmaceutically acceptable carrier, diluent or excipient, and a compound of claim 4.

12. A method of inhibiting 5α-reductase in a patient in need of such treatment comprising the administration of an effective 5α-reductase inhibiting amount of a compound of claim 1 to such patient.

13. A method of inhibiting 5α-reductase in a patient in need of such treatment comprising the administration of an effective 5α-reductase inhibiting amount of a compound of claim 2 to such patient.

14. A method of inhibiting 5α-reductase in a patient in need of such treatment comprising the administration of an effective 5α-reductase inhibiting amount of a compound of claim 3 to such patient.

15. A method of inhibiting 5α-reductase in a patient in need of such treatment comprising the administration of an effective 5α-reductase inhibiting amount of a compound of claim 4 to such patient.

* * * * *

UNITED STATES PATENT AND TRADEMARK OFFICE
CERTIFICATE OF CORRECTION

PATENT NO. : 5,430,157

DATED : July 4, 1995

INVENTOR(S) : James E. Audia

It is certified that error appears in the above-indentified patent and that said Letters Patent is hereby corrected as shown below:

Column 16, Line 5, delete "claim 2", and insert therefor --claim 1--.

Signed and Sealed this

Tenth Day of October, 1995

Attest:

BRUCE LEHMAN

Attesting Officer

Commissioner of Patents and Trademarks